United States Patent
Kokosa (10) Patent No.: US 7,178,414 B1
(45) Date of Patent: Feb. 20, 2007

(54) AUTOMATION OF LIQUID PHASE MICROEXTRACTION

(76) Inventor: John M. Kokosa, 6190 Mapleridge Dr., Flint, MI (US) 48532

( * ) Notice: Subject to any disclaimer, the term of this patent is extended or adjusted under 35 U.S.C. 154(b) by 187 days.

(21) Appl. No.: 10/788,840

(22) Filed: Feb. 27, 2004

(51) Int. Cl.
G01N 35/10 (2006.01)
G01N 1/10 (2006.01)

(52) U.S. Cl. .............................. 73/863.32; 73/864.21; 73/864.25

(58) Field of Classification Search ............. 73/863.01, 73/863.32, 864.01, 864.21, 864.91, 864.13, 73/864.22, 864.25, 864, 863.31; 422/100, 422/88, 63
See application file for complete search history.

(56) References Cited

U.S. PATENT DOCUMENTS

| | | | | |
|---|---|---|---|---|
| 3,508,442 A * | 4/1970 | Barre et al. ............... | 73/864.16 |
| 4,478,095 A | 10/1984 | Bradley et al. ........... | 73/864.21 |
| 4,713,974 A | 12/1987 | Stone ....................... | 73/864.23 |
| 4,944,781 A | 7/1990 | Ruggirello et al. ............ | 55/386 |
| 5,116,578 A | 5/1992 | Baxter .......................... | 422/63 |
| 5,324,480 A * | 6/1994 | Shumate et al. .............. | 422/63 |
| 5,441,700 A | 8/1995 | Markelov .................... | 422/83 |
| 5,531,959 A * | 7/1996 | Johnson et al. ............... | 422/70 |
| 5,691,206 A | 11/1997 | Pawliszyn ................... | 436/178 |
| 5,760,299 A * | 6/1998 | Johnson et al. ............ | 73/61.56 |
| 5,792,423 A | 8/1998 | Markelov .................... | 422/83 |
| 5,861,563 A | 1/1999 | Boyd et al. ............... | 73/864.21 |
| 5,948,360 A | 9/1999 | Rao et al. ..................... | 422/65 |
| 5,969,813 A | 10/1999 | Hammond et al. ......... | 356/319 |
| 6,143,573 A | 11/2000 | Rao et al. ................... | 436/180 |
| 6,146,895 A | 11/2000 | Green et al. ................. | 436/47 |
| 6,164,144 A | 12/2000 | Berg ........................ | 73/863.21 |
| 6,286,375 B1 | 9/2001 | Ward ....................... | 73/863.12 |
| 6,405,608 B1 | 6/2002 | Lindgren et al. ......... | 73/863.21 |
| 6,426,225 B1 | 7/2002 | Lewis et al. .................... | 436/8 |
| 6,537,827 B1 | 3/2003 | Pawliszyn .................... | 436/178 |
| 6,662,626 B2 * | 12/2003 | van der Maas ............ | 73/23.35 |
| 2002/0006360 A1 | 1/2002 | Neal et al. ................... | 422/100 |
| 2002/0157453 A1 * | 10/2002 | van der Maas ............ | 73/23.35 |
| 2002/0176799 A1 | 11/2002 | McCorkle ..................... | 422/64 |
| 2002/0190202 A1 | 12/2002 | Liang ......................... | 250/288 |
| 2003/0222007 A1 | 12/2003 | Gu et al. .................. | 210/198.2 |
| 2005/0150314 A1 * | 7/2005 | Staples et al. ........... | 73/863.01 |

FOREIGN PATENT DOCUMENTS

WO    WO 9725606 A1 *   7/1997

OTHER PUBLICATIONS

LEAP Technologies, PAL Training Check List.
Kettering University Science & Mathematics Department, Headspace Solvent Microextraction—a Novel Preparation Technique for Environmental Samples.

(Continued)

Primary Examiner—Hezron Williams
Assistant Examiner—Tamiko Bellamy
(74) Attorney, Agent, or Firm—Young Basile Hanlon MacFarlane & Helmholdt (57) ABSTRACT

A method and apparatus for automatically performing liquid microextraction on liquid samples includes the steps of controlling movement of a syringe between a cleaning station, a sample station containing a plurality of discrete sample vials and an instrument injector station. Movement of the syringe is controlled automatically for cleaning the syringe, obtaining a sample of each sample in each discrete sample vial, one at a time, and injecting the collected sample into the instrument injector, and then repeating the sequence steps for all discreet samples.

13 Claims, 10 Drawing Sheets

OTHER PUBLICATIONS

John M. Kokosa & Andrzej Pryjazny, Headspace Microdrop Analysis—An Improved Test Method for Gasoline Diluent in Used Engine Oils.

LEAP Technologies, Single Magnet Mixer for SPME Applications.

Combi PAL Operating Manual.

Varian Analytical Instruments, Combi PAL SPME Manual.

Kihwan Choi, Yongseong Kim, and Doo Soo Chung, Liquid-Phase Microextraction as an On-line Preconcentration Method in Capillary Electrophoresis.

Xiujuan Wen, Chuanhong Tu, and Hian Kee Lee, Two-Step Liquid-Liquid-Liquid Microextraction of Nonsteroidal Antiinflammatory Drugs in Wastewater.

John M. Kokosa & Andrzej Pryjazny, Headspace Microdrop Analysis—An Alternative Test Method for Gasoline Diluent and Benzene, Toluene, Ethylbenzene, and Xylenes in Used Engine Oils, 2002.

Elefteria Psillakis & Nicolas Kalogerakis, Application of Solvent Microextraction to the Analysis of Nitroaromatic Explosives in Water Samples, 2001.

Limian Zhao & Hian Kee Lee, Application of Static Liquid-phase Microextraction to the Analysis of Organochlorine Pesticides in Water, 2001.

Limian Zhao & Hian Kee Lee, Determination of Phenols in Water Using Liquid Phase Microextraction with Back Extraction Combined with High-Performance Liquid Chromatography, 2001.

Lowri S. de Jager & Anthony R. J. Andrews, Development of a Screening Method for Cocaine and Cocaine Metabolites in Urine Using Solvent Microextraction in Conjunction with Gas Chromatography, 2001.

Lingyan Zhu, Liang Zhu, & Hian Kee Lee, Liquid-Liquid-Liquid Microextraction of Nitophenols with a Hollow Fiber Membrane Prior to Capillary Liquid Chromatography, 2001.

Trine Grohaug Halvorsen, Stig Pedersen-Bjergaard, & Knut E. Rasmussen, Liquid-Phase Microextraction and Capillary Electrophoresis of Citalopram, and Antidepressant Drug, 2001.

Trine Grohaug Halvorsen, Stig Pedersen-Bjergaard, & Knut E. Rasmussen, Reduction of Extraction Times in Liquid-Phase Microextraction, 2001.

Kirsten E. Kramer & Anthony R. J. Andrews, Screening Method for 11-nor-$\Delta^9$-tetrahydrocannabinol-9-carboxylic acid in Urine Using Hollow Fiber Membrane Solvent Microextraction with In-tube Derivatization, 2001.

Elefteria Psillakis & Nicolas Kalogerakis, Solid-Phase Microextraction Versus Single-Drop Microextraction for the Analysis pf Nitroaromatic Explosives in Water Samples, 2001.

Aaron L. Theis, Adam J. Waldack, Susan M. Hansen, & Michael A. Jeannot, Headspace Solvent Microextraction, 2001.

Hongyan Zhang & Anthony R. J. Andrews, Preliminary Studies of a Fast Screening Method for Polycyclic Aromatic Hydrocarbons in Soil by Using Solvent Microextraction-Gas Chromatography, 2001.

Wuping Liu & Hian Kee Lee, Continuous-Flow Microextraction Exceeding 1000-Fold Concentration of Dilute Analytes, 2000.

T. Ligor & B. Buszewski, Extraction of Trace Organic Pollutants from Aqueous Samples by a Single Drop Method, 2000.

Lowri S. de. Jager & Anthony R. J. Andrews, Development of a Rapid Screening Technique for Organochlorine Pesticides Using Solvent Microextraction (SME) and Fast Gas Chromatography, 2000.

Andrzej Przyjazny, Joel F. Austin, & Andrew T. Essenmacher, Headspace Liquid-Phase Microextraction—A Novel Preconcentration Technique for Volatile Organic Pollutants.

L.S. Jager & A.R.J. Andrews, Solvent Microextraction of Chlorinated Pesticides, 1999.

Yan Wang, Yien Chian Kwok, Yan He, & Hian Kee Lee, Application of Dynamic Liquid-Phase Microextraction to the Analysis of Chlorobenzenes in Water by Using a Conventional Microsyringe, 1998.

Y. He & H. K. Lee, Liquid-Phase Microextraction in a Single Drop of Organic Solvent by Using a Conventional Microsyringe, 1997.

Michael A. Jeannot & Frederick F. Cantwell, Solvent Microextraction as a Speciation Tool: Determination of Free Progesterone in a Protein Solution, 1997.

Michael A. Jeannot & Frederick F. Cantwell, Mass Transfer Characteristics of a Solvent Extraction into a Single Drop at the Tip of a Syringe Needle, 1997.

Michael A. Jeannot & Frederick F. Cantwell, Solvent Microextraction into a Single Drop, 1996.

Hanghui Liu & Puernendu K. Dasgupta, Analytical Chemistry in a Drop. Solvent Extraction in a Microdrop, 1996.

Standard Test Method for Gasoline Diluent in Used Gasoline Engine Oils by Gas Chromatography.

* cited by examiner

AUTOMATION OF LIQUID PHASE MICROEXTRACTION

BACKGROUND

The present invention relates, in general, to autosamplers for use with chemical separation and analysis methods which have means for identifying the separated components: gas chromatography, gas chromatography mass spectroscopy and high performance liquid chromatography, to name a few.

During the last eight years, a new concept for concentrating analytes for analysis has been developed. The most widely accepted generic term for this methodology is "Liquid Phase Microextraction or LPME". The technique involves the use of 1–5 microliters of solvent to concentrate chemicals present in water, air or the head space atmosphere above a liquid or solid sample. After the chemicals are concentrated from the medium into the solvent, the liquid is injected into an appropriate chromatography instrument for separation and analysis, or directly analyzed if component separation is not necessary.

The applications of this technique are wide-ranging and growing. The method has been used to analyze pharmaceuticals and environmental contaminants in blood, organic environmental chemicals in water, and solvents and impurities in solids, to name a few examples.

LPME can be used with almost any analytical method, including GG, GC/MS, HPLC, Capillary Electrophoresis separation-analysis methods, or without separation techniques using FTIR, UV/VIS, NMR or MS. LPME and Microdrop Head Space Analysis (or MDHA) techniques allow dilute or even relatively concentrated samples in complex sample matrices to be concentrated into a small solvent volume for analysis.

The general procedure for LPME involves the following steps: 1) a solvent is drawn into a sampling device, commonly a syringe or adapted syringe-like device, 2) a microdrop of the solvent is then forced out of the syringe onto the tip of the syringe needle and into the medium to be sampled, 3) the chemicals of interest are partitioned into the solvent over a period of a few minutes, and 4) the solvent microdrop is withdrawn into the syringe and the sample concentrate then analyzed.

The solvent microdrop can be exposed directly to the sample medium, or it can be encased in a polymeric hollow fiber or film which is immersed in the medium and into which the sample can also partition into. The latter method protects the microdrop from being removed from the needle tip during the sampling period. As with all sampling techniques, in order to obtain good reproducible analytical results with this method, the timing and precision of each of the above steps must be reproducible. To this point, this method has suffered from the lack of automated reproduction of these manual steps.

A number of manufacturers sell autosamplers which can perform multiple injections in gas chromatography or liquid chromatography of varying sample volumes. However, such autosamplers and automation methods have been employed only with the insertion of the syringe into the sample and the extraction of a portion of the sample into the syringe. Heretofore, there has not been an automated method for liquid phase microextraction thereby requiring the manual ejecting of a microdrop of a solvent out of the syringe and onto the tip of the syringe needle in the head space above the sample or into the medium to be sampled. This is a tedious task when numerous samples must be analyzed and requires precise and continued plunger control to maintain the microdrop on the tip of the plunger for the sample period. This is a difficult manual task, especially for numerous samples.

Thus, it would be desirable to provide automated reproduction of liquid phase microextraction methodology or process steps. It would also be desirable to provide an automated method for liquid phase microextraction which can be easily implemented in existing autosampling equipment.

SUMMARY

The present invention is an apparatus and method for automation of liquid phase microextraction for use in gas chromatography and chemical separation and analysis methods such as gas chromatography, high performance liquid chromatography and mass chromatography mass spectroscopy (GC HPLC GC/MS).

In one aspect, the present invention is a method for automatically performing liquid microextraction analysis of a plurality of samples in separate vials.

The method comprises the steps of:
controlling movement of a syringe in multiple axes;
cleaning the syringe;
drawing a carrier liquid into the syringe;
moving the syringe to a sample vial;
inserting a tip of the syringe into the vial;
collecting a portion of the sample in the syringe;
withdrawing the syringe from the sample vial;
moving the syringe to an instrument injector;
injecting the sample into the instrument injector for analysis of the sample; and
repeating the prior steps on each of the plurality of samples.

The step of inserting further comprises the steps of activating a syringe plunger to expel and hold a microdrop of the solvent on the tip of the syringe, holding the microdrop on the tip of the syringe in the sample vial for a period of time to collect the sample, and drawing the microdrop and the collected portion of the sample into the syringe.

In another aspect, the method steps include placing a plurality of sample vials in a holder in established coordinate positions.

In yet another aspect, the method steps include:
providing a syringe cleaning solution in a known coordinate position;
moving the syringe to the cleaning vial and withdrawing contents of the cleaning solution into the syringe; and
expelling the cleaning solution from the syringe into a waste receptacle.

In another aspect, the method includes the step of inserting the syringe into the sample vial to position the tip of the syringe in a head space above a liquid sample in the vial, or inserting the tip of the syringe into the liquid sample in the sample vial.

The present apparatus also includes:
an apparatus for automatically performing liquid microextraction analysis of a plurality of samples in separate vials, the apparatus comprises:
means for controlling movement of a syringe in multiple axes;
means for cleaning the syringe;
means for drawing a carrier liquid into the syringe;
means for moving the syringe to a sample vial;
means for inserting a tip of the syringe into the vial;

means for collecting a portion of the sample in the syringe;

means for withdrawing the syringe from the sample vial;

means for moving the syringe to an instrument injector;

means for injecting the sample into the instrument injector for analysis of the sample.

The apparatus and method of the present invention uniquely automates liquid phase microextraction of a plurality of samples.

BRIEF DESCRIPTION OF THE DRAWING

The various features, advantages and other uses of the present invention will become more apparent by referring to the following detailed description and drawing in which.

DETAILED DESCRIPTION

Refer now to the drawing, and to FIGS. 1–9, in particular, there is depicted an apparatus 10 for performing automatic gas chromatography. The apparatus 10 includes a gas chromatograph 12 and an autosampler 14. The autosampler 14 is mounted on the gas chromatograph 12.

Figure 1:
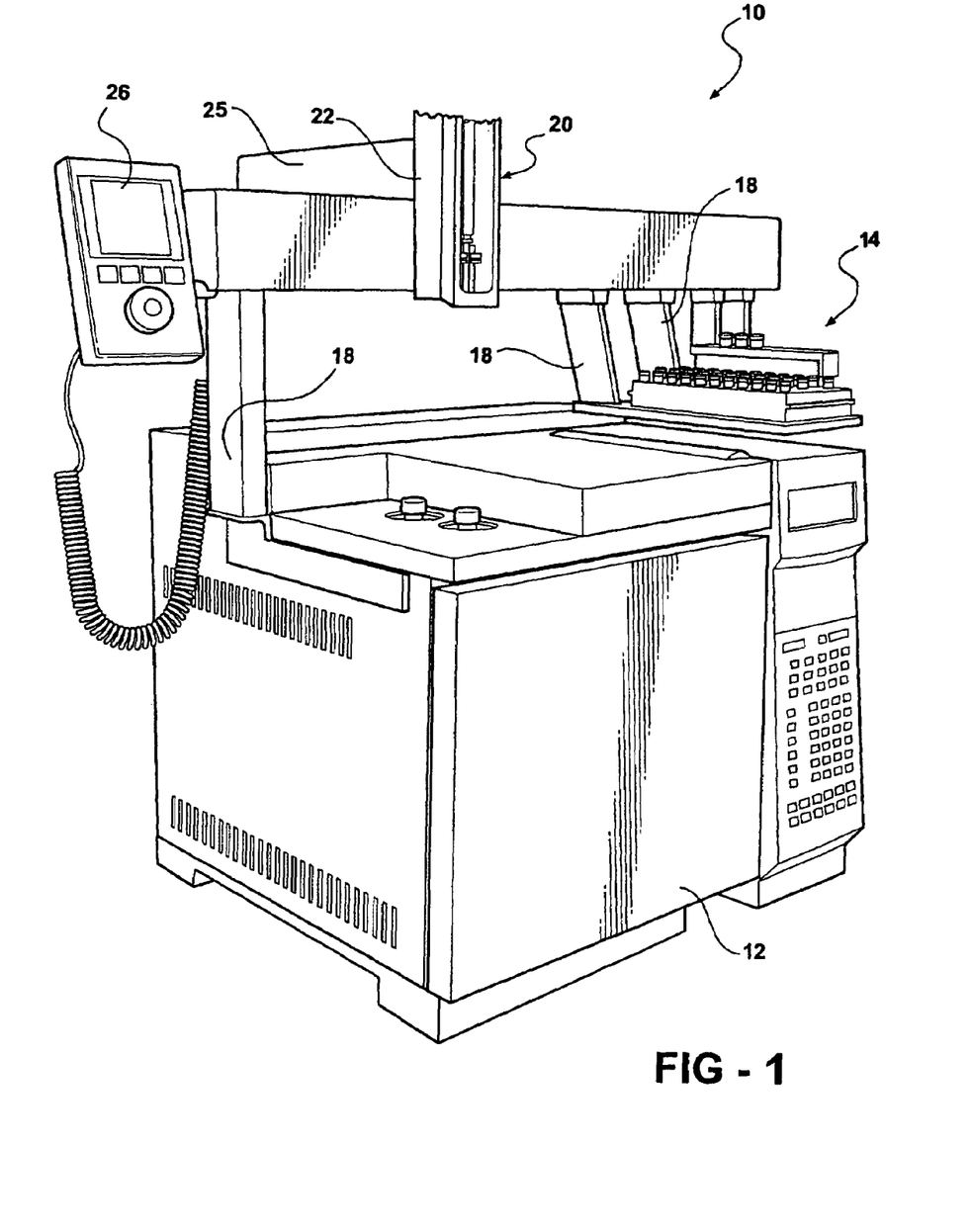
FIG. 1 is a perspective view of a autosampler and gas chromotagraph which can be used to implement the present apparatus and method.
Figure 2:
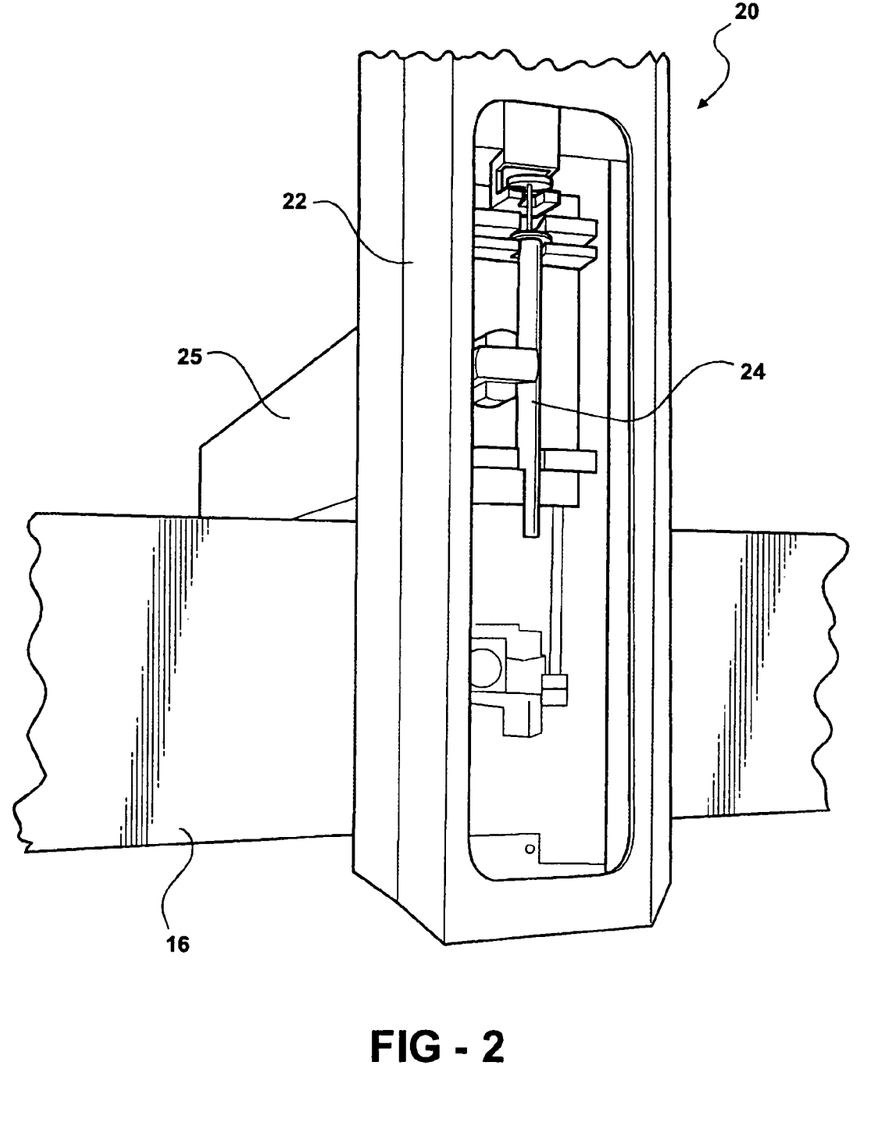
FIG. 2 is an enlarged, partial perspective view of the injector of the autosampler shown in FIG. 1.

The autosampler 14 includes a frame 16 having support legs 18 attachable to the housing of the gas chromatograph 12. The frame 16 defines a horizontal track for an injector assembly 20. The injector assembly 20 includes a housing 22 supporting at least one injector, such as a syringe 24.

The autosampler 14 may be any suitable autosampler 14 used in gas chromatography or mass spectronomy. By example only, the autosampler 14 can be a Combi PAL manufactured by CTC Analytics, AG, Germany.

The injector assembly 20 is mounted on a track 25 for movement along a Y axis relative to the frame or horizontal track 16. The injector assembly 20 also contains controls and drive elements for moving the syringe 24 in a Z axis relative to the frame or horizontal track 16.

A control means or controller 26 is mounted on the frame 16 and includes suitable input devices and an output display for entering commands and displaying messages, sequence steps, etc., for controlling the operation of the autosampler 14. The controller 26 includes a central processing unit which executes instructions stored as macros in a memory for controlling the operation of the autosampler 14, as described hereafter.

Figure 3:
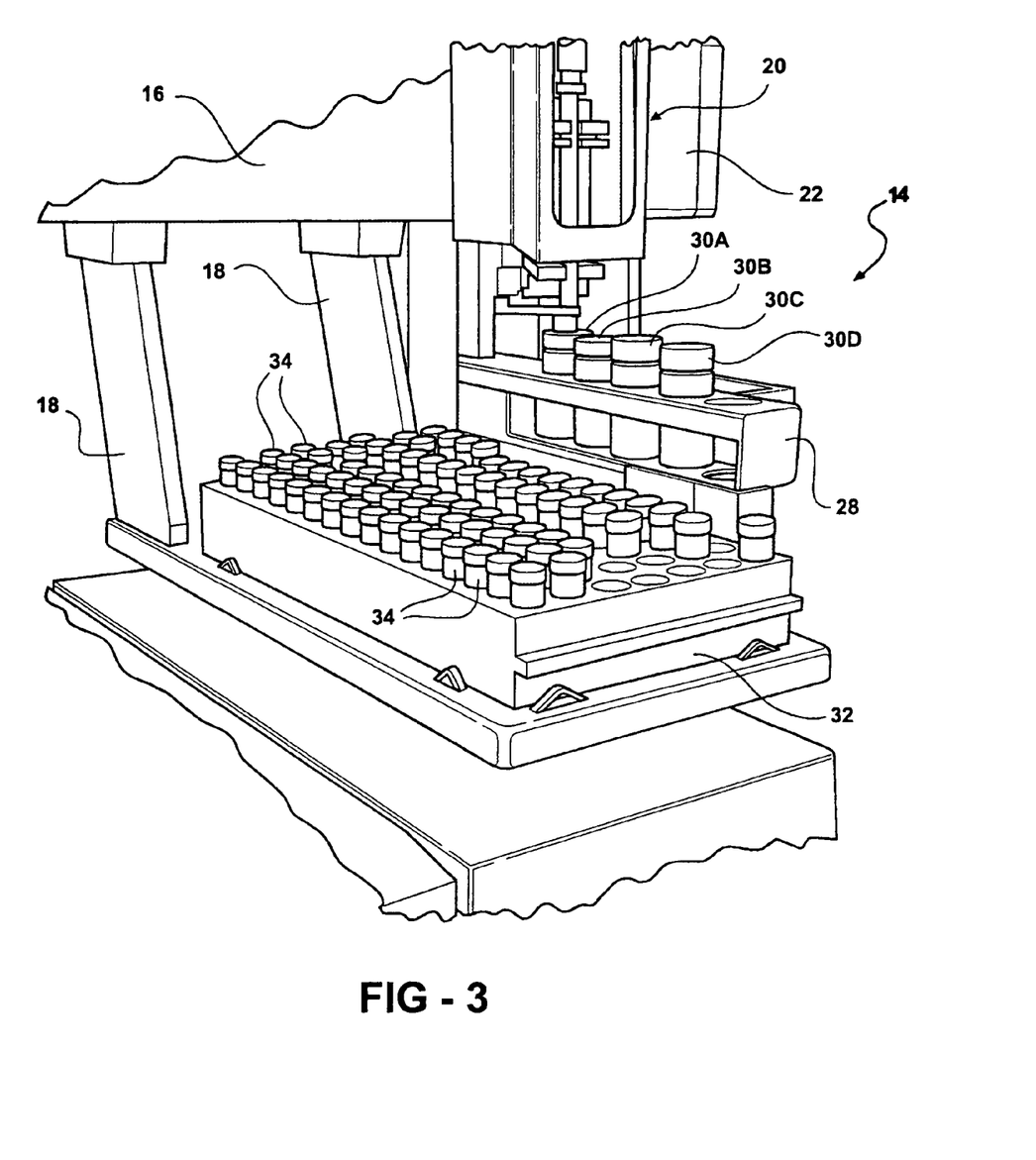
FIG. 3 is an enlarged, partial, perspective view of the cleaning and carrier tray of the sample holder of the autosampler shown in FIG. 1.

Also supported on the frame 16 is a first tray 28 containing a plurality of vials, with four vials 30A, 30B, 30C, and 30D being shown by way of example only. The vials 30A–30D are provided for a sample carrier or solvent, and cleaning solutions as described hereafter.

Also mounted on the frame 16 is a second specimen or sample holder 32. The holder 32 is configured for holding a plurality of sample vials 34 which contain samples to be tested in the gas chromatograph 12.

In normal operation, the autosampler 14 operates to bring the injector assembly 20 to a position over one of the sample vials 34 in the holder 32. The syringe 24 is lowered to cause the tip of the syringe 24 to pierce the septum of one vial 34 to extract a sample from the material in the vial 34. This specific extraction technique will be described hereafter.

The injector assembly 24 then elevates the syringe 24 and traverses along the frame 16 and along the Y axis track 25, as necessary, to move the injector assembly 20 over one of the injectors 36 and 38 of the gas chromatograph 12. The syringe 24 is lowered to cause the tip of the syringe 24 to pierce the septum on one of the injectors 36 and 38 of the gas chromotagraph 12 before the plunger of the syringe 24 is depressed to inject the contents of the syringe 24 into the injector 36 or 38 for analysis of the contents of the sample.

According to the present invention, the autosampler 14 includes a, such as the Combi PAL described above, a member of control programs or "macros" stored in a memory of the controller 26 for automating liquid microextraction of a plurality of samples in the holder 32 continuously and automatically until all of the samples are tested.

The macros can be non-permanently modified for an analysis. The controller 26 also stores information on any attachments, such as the first tray 28 and the holder 32, being used and their location.

A software program is also available which contain the actual macro programming capabilities to modify an auto-sampling method or to program the LPME method.

Various commands are available in the macro-programming software for controlling all aspects of the operation of the autosampler 14, including injector movement, injector volume and injector speed, agitation time, incubation time, wash cycle variables, etc. The available software commands are used to create the macro program which implements the following method of operation of the autosampler 14 in automating liquid microextraction.

When operating, the software named Cycle Composer in the Combi PAL auto-sampler 14, the computer downloads all of the information stored in the controller 26 and takes direct control of the auto-sampler 14. Alternately, the complete LPME macro could be developed and stored in the controller 26.

The method employed by the present invention is executed by the macro program and involves a first step of cleaning the syringe 24. The syringe 24 is moved over the vial 30A, for example, in the first tray 28, and as shown in FIG. 3 extract lowered to a cleaning agent from the vial 30A.

Figure 4:
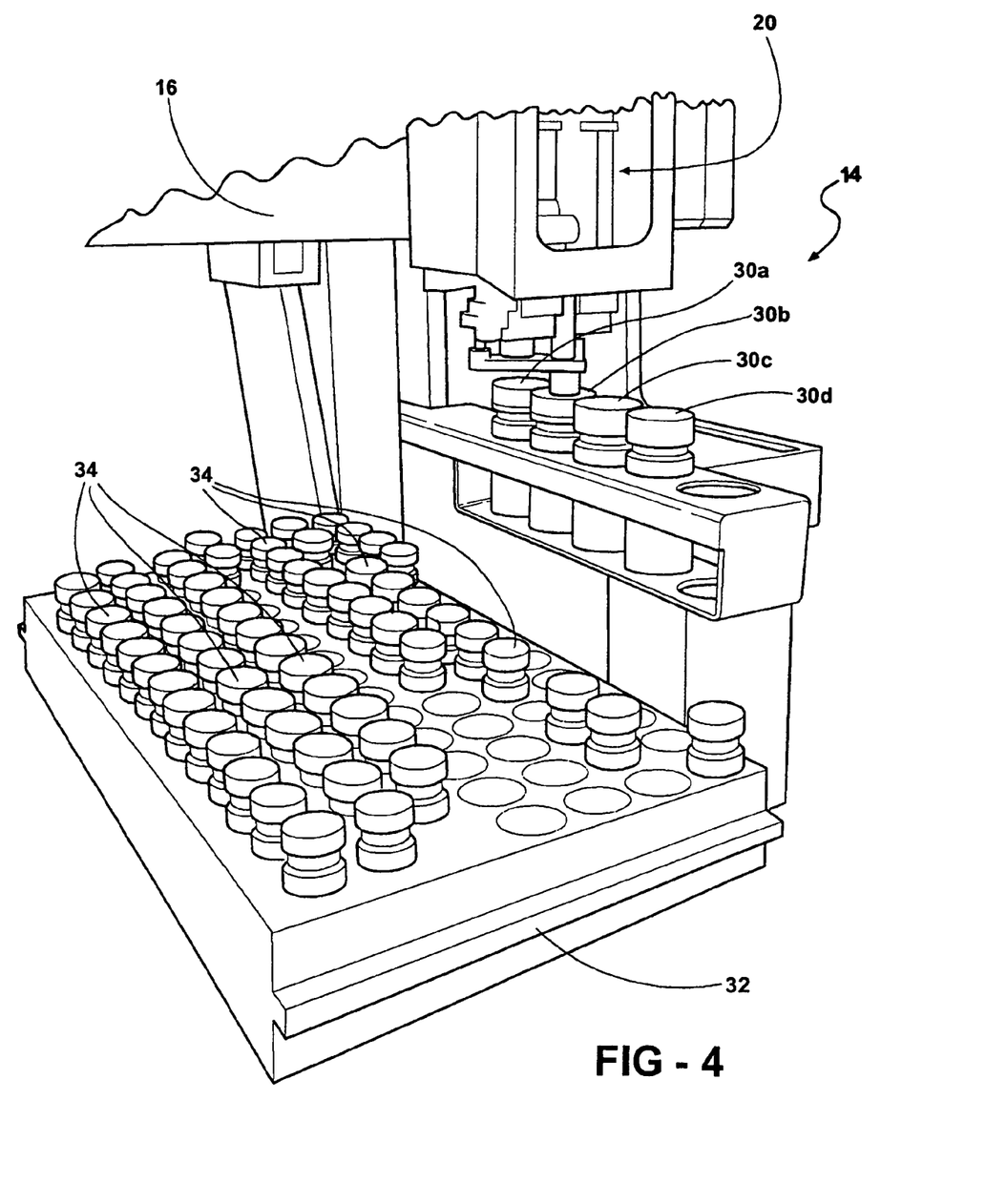
FIGS. 4–6 are partial, enlarged, perspective views showing the sequence of movement of the injector between the cleaning and sample carrier vials shown in FIGS. 1 and 3.
Figure 5:
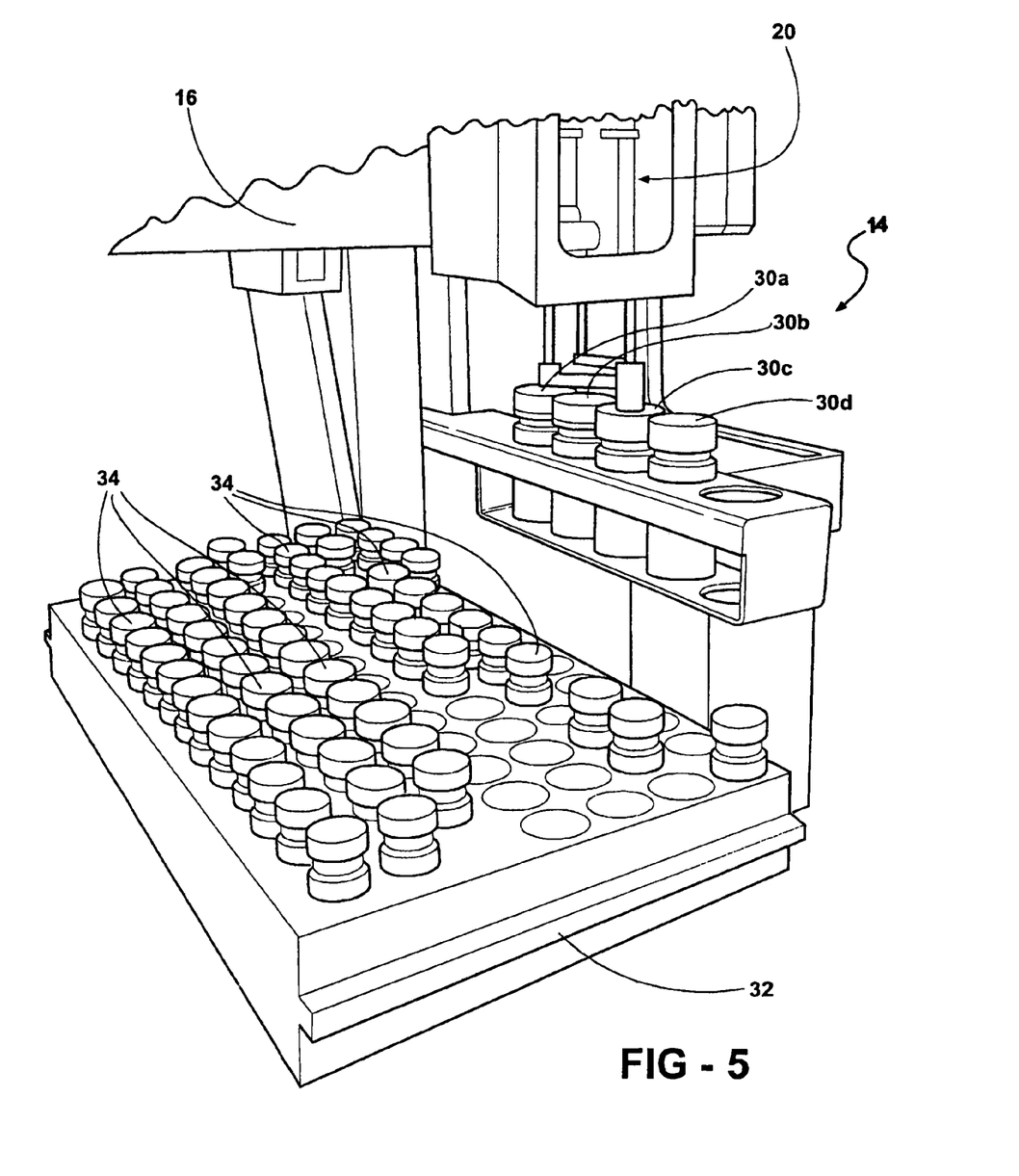

The syringe 24 is then moved over the second vial 30B as shown in FIG. 4 wherein the cleaning agent and any remaining previous sample in the syringe 24 are expelled into the second vial 30B. The third vial 30C may be employed for an additional cleaning agent, if necessary. The use of any cleaning agent in the third vial 30C, FIG. 5, can be expelled into the second vial 30B as described above.

Figure 6:
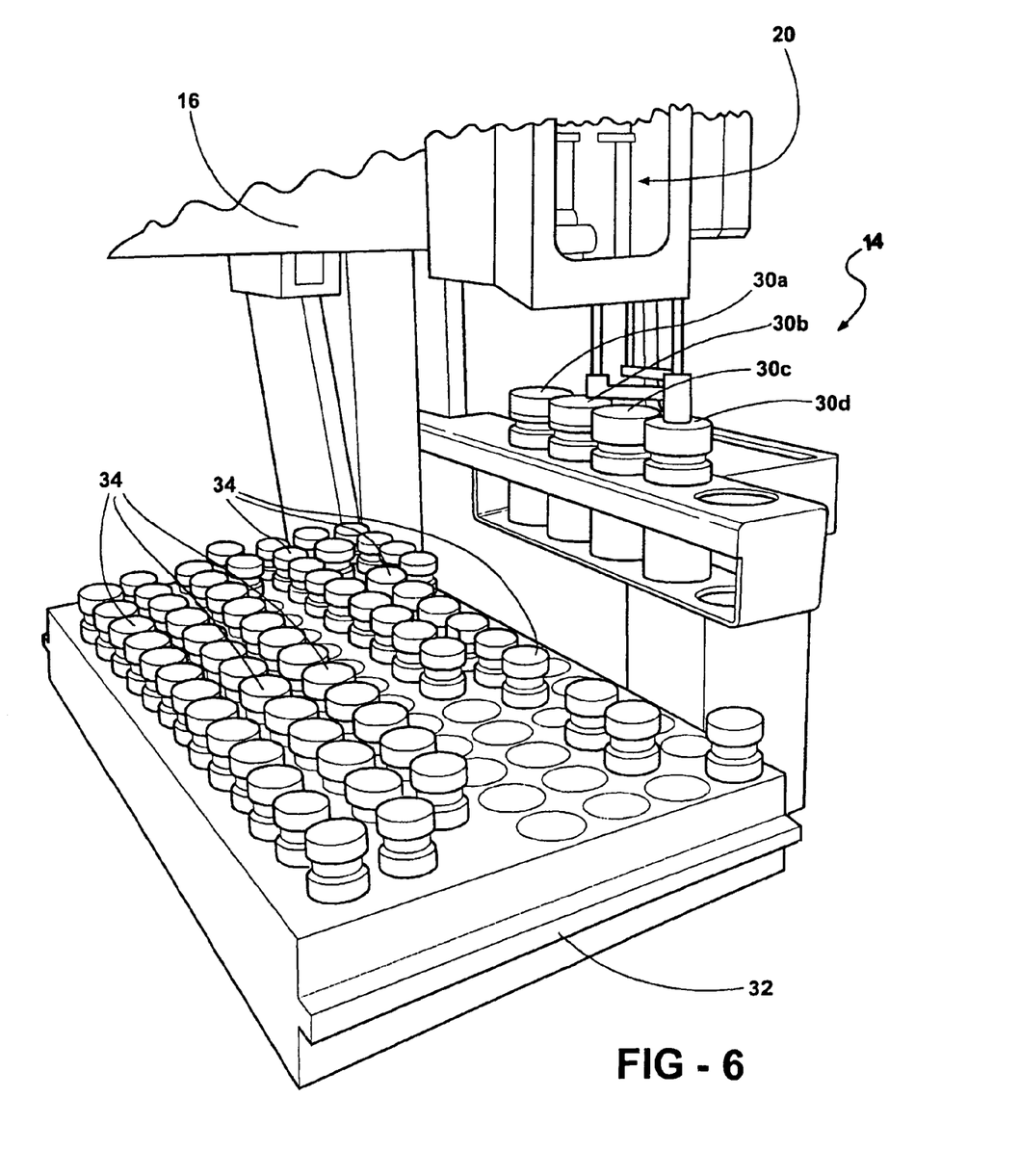

The fourth vial 30D contains sampling solvent in which a small volume of sample solvent, such as hexadecane by example only, is drawn into the syringe 24 for each sample sequence, as shown in FIG. 6.

Figure 7:
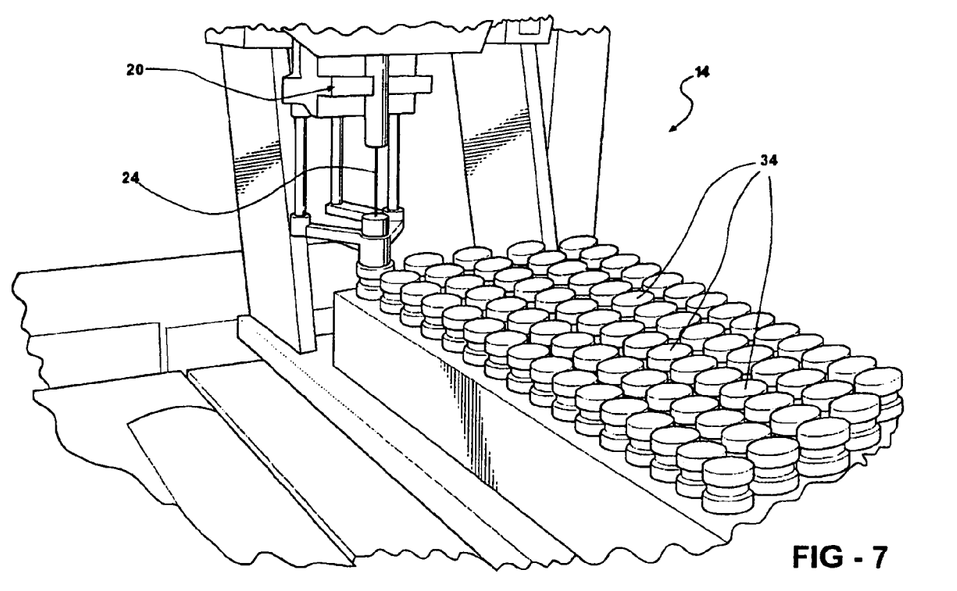
FIG. 7 is an enlarged, partial, perspective view showing the injector engaged with one of the sample vials.

The autosampler 14 then moves the entire injector assembly 20, as shown in FIG. 7, to a position locating the syringe 24 over one of the sample vials 34 in the holder 32. The syringe 24 lowers a prescribed distance to cause the tip of the syringe 24 to pierce the septum in the selected sample vial 34.

Next, the syringe plunger is activated to expel a microdrop of the solvent on the tip of the syringe 24. As occurs in liquid micro extraction, the microdrop is maintained on the tip of the syringe 24 and collects sample material in the head space above the fluid sample in the vial 34. The microdrop is maintained on the tip of the syringe 24 for a predetermined time period as set in the macroprogram. A three minute sample period can be used by way of example only.

Next, the microdrop is drawn back into the syringe 24 by movement of the syringe plunger.

Figure 8:
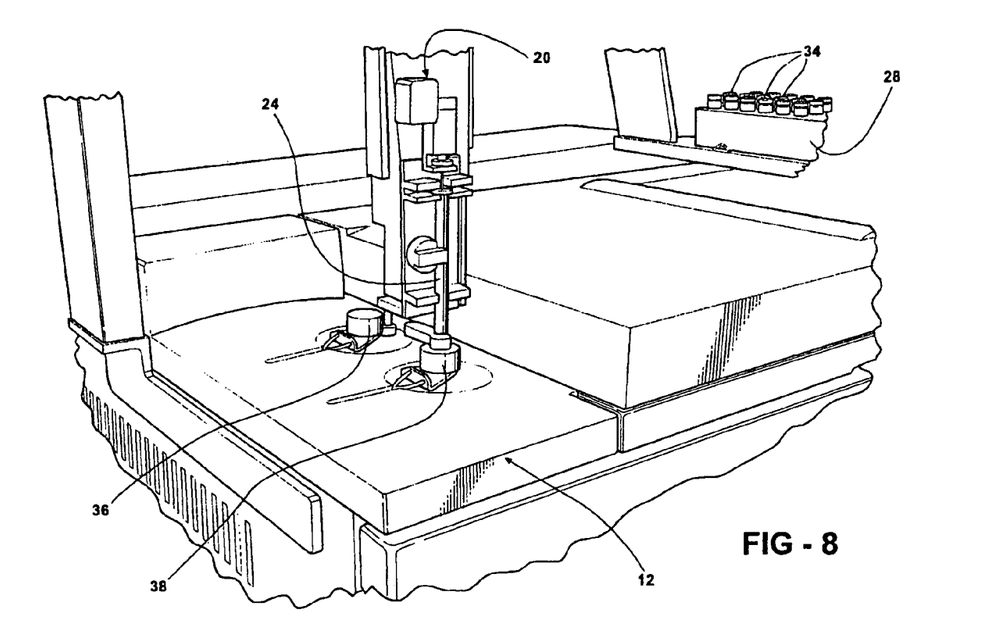
FIG. 8 is a perspective view showing the engagement of the injector syringe with the injector port of the gas chromotagraph shown in FIG. 1.

The injector assembly 20 is then moved over one of the injectors 36 or 38 of the gas chromotagraph 12 as shown in FIG. 8. The syringe 24 is lowered until the tip of the syringe 24 pierces the septum in the selected injector 36 or 38. The plunger is then depressed to expel at least a portion of the contents of the syringe 24 into the selected injector 36 or 38 of the gas chromatograph for analysis.

The syringe 24 is then withdrawn from the injector 36 or 38 and the process repeated through cleaning, drawing in new solvent, liquid microextraction in the head space of the next sample vial 34, and injection into one of the gas chromatograph injectors 36 or 38.

Figure 9:
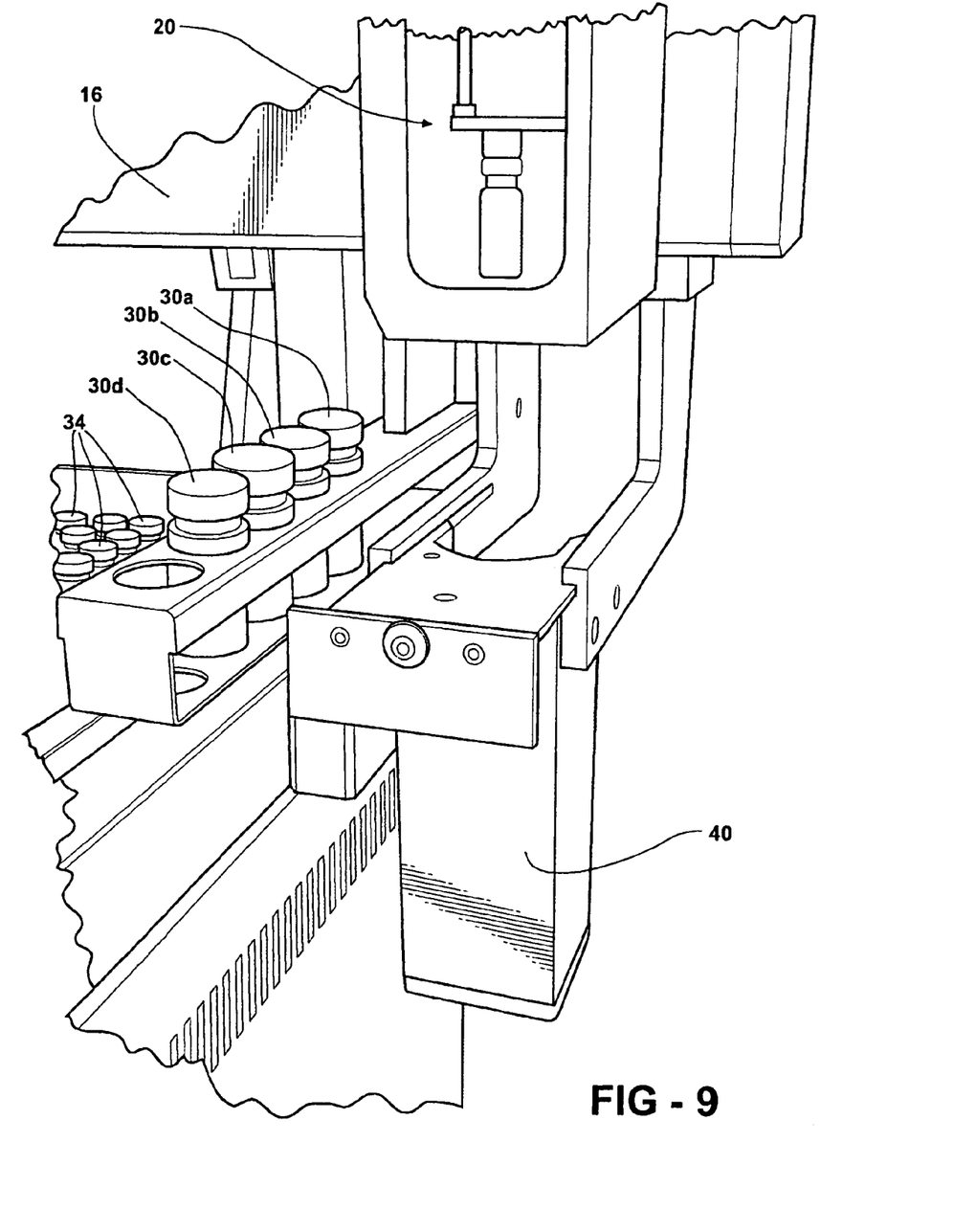
FIG. 9 is an enlarged, partial, perspective view showing an alternate sample agitator/heater which can be used in the autosampler apparatus and method of the present invention.

The above-described automated liquid microextraction process can also be modified for introducing a step into the automated process in which the contents of any vial 34 or any sample drawn into the syringe 24 may be agitated in an agitator device 40 shown in FIG. 9. The agitator device 40 is a commercially available agitator mounted by supports to the frame 16 of the autosampler 14.

Figure 10:
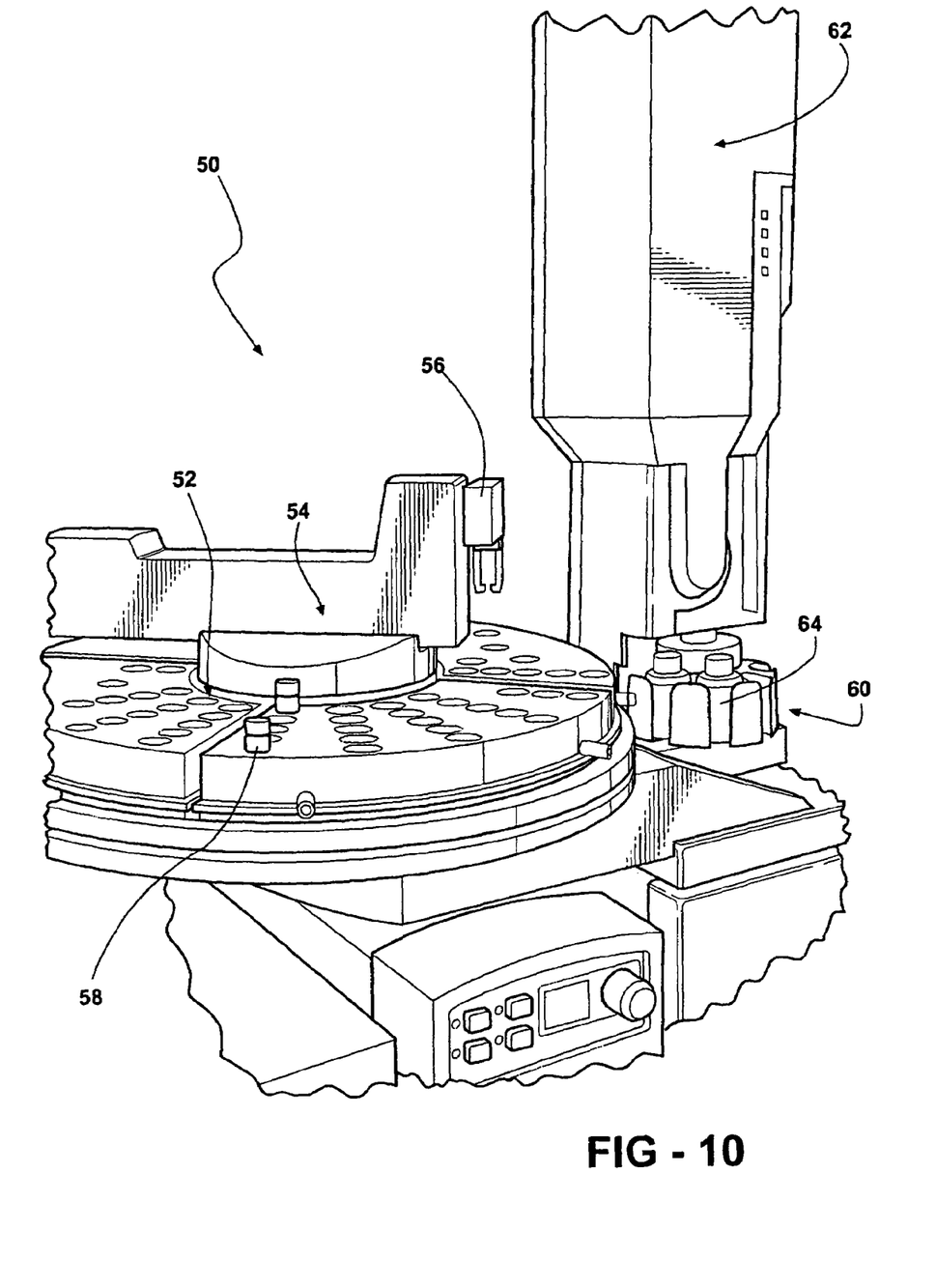
FIG. 10 is a perspective of an alternate autosampler which can implement the sampling apparatus and method of the present invention.

The present automated liquid microextraction process may also be used in other types of autosamplers, such as the autosampler 50 shown in FIG. 10. The autosampler 50 is an agilent 7683 Series injector, by example only.

This type of autosampler 50 includes a carousel 52 containing a plurality of vials arranged in radially extending rows. A selector assembly 54 is mounted on the carousel 52 and contains a gripper 56 for selecting one of a plurality of vials 58 in the carousel 52. The gripper 56 is moveable along an axis from the carousel 52 to a rotary holder 60 positioned below an stationary injector assembly 62. The gripper 56 is operative to insert or withdraw one of the vials 58 into or out of the holder 60. Other vials 64 carried in the holder 60 contain cleaning media, sample solvent and a waste receptacle for cleaning the syringe carried in the injector assembly 62 in a similar manner as that described above.

The control of the autosampler 50 is performed by a macro program in the control means which functions in a manner similar to the method described above to automate the liquid microextraction of multiple samples and an analysis of the samples in a gas chromotagraph, etc.

In summary, the present invention is a method for automating liquid microextraction of multiple samples in chemical separation and analysis methods, such as GC HPLC GC/MS.

What is claimed is:

1. A method of automatically performing liquid microextraction analysis on a plurality of samples in separate vials comprising the steps of:
    controlling movement of a syringe in multiple axes;
    cleaning the syringe;
    drawing a carrier solvent into the syringe;
    moving the syringe to a sample vial;
    inserting a tip of the syringe into the sample vial;
    activating a syringe plunger to expel and hold a microdrop of the solvent on the tip of the syringe;
    holding the microdrop on the tip of the syringe in the sample vial for a period of time to collect the sample material in a space above the sample in the vial;
    drawing the microdrop and the collected portion of the sample into the syringe;
    withdrawing the syringe from the sample vial;
    moving the syringe to an instrument injector;
    injecting the sample into the instrument injector for analysis of the sample; and
    repeating the prior steps on each of the plurality of samples.

2. The method of claim 1 further comprising the step of:
    placing a plurality of sample vials in a holder in established coordinate positions.

3. The method of claim 1 further comprising the step of:
    providing a syringe cleaning solution in a known coordinate position.

4. The method of claim 3 wherein the step of cleaning the syringe comprises the steps of:
    moving the syringe to the cleaning vial and withdrawing contents of the cleaning solution into the syringe; and
    expelling the cleaning solution from the syringe into a waste receptacle.

5. The method of claim 1 wherein the step of inserting the syringe into the sample vial further comprises the step of:
    inserting the syringe into the sample vial to position the tip of the syringe in a head space above a liquid sample in the vial.

6. The method of claim 1 wherein the step of inserting the syringe into the sample vial further comprises the step of:
    inserting the tip of the syringe into the liquid sample in the sample vial.

7. An apparatus for automatically performing liquid microextraction analysis of a plurality of samples in separate vials, the apparatus comprising:
    means for controlling movement of a syringe in multiple axes;
    means for cleaning the syringe;
    means for drawing a carrier solvent into the syringe;
    means for moving the syringe to a sample vial;
    means for inserting a tip of the syringe into the sample vial;
    means for collecting a portion of the sample in the syringe, the collecting means further comprising:
        means for activating a syringe plunger to expel and hold a microdrop of the solvent on the tip of the syringe;
        means for holding the microdrop on the tip of the syringe in the sample vial for a period of time to collect the sample material in a space above the sample in the vial; and
        means for drawing the microdrop and the collected portion of the sample into the syringe;
    means for withdrawing the syringe from the sample vial;
    means for moving the syringe to an instrument injector;

means for injecting the sample into the instrument injector for analysis of the sample.

8. A method of automatically performing liquid microextraction analysis on a plurality of samples in separate vials comprising:
controlling movement of a syringe and sample vial in multiple axes relative to one another;
cleaning the syringe;
drawing a carrier solvent into the syringe;
moving the syringe and sample vial relative to one another;
inserting a tip of the syringe into the sample vial;
activating a syringe plunger to expel and hold a microdrop of the solvent on the tip of the syringe;
holding the microdrop on the tip of the syringe in the sample vial for a period of time to collect the sample material in a space above the sample in the vial;
drawing the microdrop and the collected portion of the sample into the syringe;
withdrawing the syringe from the sample vial;
moving the syringe and an instrument injector relative to one another;
injecting the sample into the instrument injector for analysis of the sample; and
repeating the prior steps on each of the plurality of samples.

9. The method of claim 8 further comprising the step of:
placing a plurality of sample vials in a holder in established coordinate positions.

10. The method of claim 8 further comprising the step of:
providing a syringe cleaning solution in a known coordinate position.

11. The method of claim 10 wherein the step of cleaning the syringe comprises the steps of:
moving the syringe and the cleaning vial relative to one another and withdrawing contents of the cleaning solution into the syringe; and
expelling the cleaning solution from the syringe into a waste receptacle.

12. The method of claim 8 wherein the step of inserting the syringe into the sample vial further comprises the step of:
inserting the syringe into the sample vial to position the tip of the syringe in a head space above a liquid sample in the vial.

13. The method of claim 8 wherein the step of inserting the syringe into the sample vial further comprises the step of:
inserting the tip of the syringe into the liquid sample in the sample vial.

* * * * *